United States Patent
Ono et al.

(10) Patent No.: US 7,067,514 B2
(45) Date of Patent: Jun. 27, 2006

(54) PYRIMIDINE COMPOUNDS

(75) Inventors: Mitsunori Ono, Lexington, MA (US);
Shijie Zhang, Nashua, NH (US);
Teresa Przewloka, Tewksbury, MA (US); Keizo Koya, Chestnut Hill, MA (US); Elena Kostik, Arlington, MA (US); Yuniko Wada, Waltham, MA (US); Lijun Sun, Harvard, MA (US);
Weiwen Ying, Ayer, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 68 days.

(21) Appl. No.: 10/656,671

(22) Filed: Sep. 5, 2003

(65) Prior Publication Data

US 2004/0048873 A1 Mar. 11, 2004

Related U.S. Application Data

(63) Continuation of application No. 10/000,742, filed on Nov. 30, 2001, now Pat. No. 6,693,097.

(51) Int. Cl.
A61K 31/506 (2006.01)
A61P 3/10 (2006.01)
A61P 17/06 (2006.01)
A61P 19/02 (2006.01)
A61P 25/28 (2006.01)

(52) U.S. Cl. .................. 514/227.8; 514/235.8; 514/252.14; 514/269; 514/275

(58) Field of Classification Search ............ 514/252.14, 514/269, 275, 235.8, 227.8
See application file for complete search history.

(56) References Cited

U.S. PATENT DOCUMENTS 6,384,032 B1  5/2002 Ono et al. ................. 514/241

OTHER PUBLICATIONS

Trincheri, Current Opinion in Hematology 4: 59–66, 1997.*
Arvanitis, et al. *Non–Peptide Corticotropin–Releasing Hormone Antagonists: Syntheses and Structure—Activity Relationships of 2–Anilinopyrimidines and –triazines.* J. Med. Chem, vol. 42, 1999, pp. 805–818.

Mylari, et al. *Sorbitol Dehydrogenase Inhibitors (SDIs): A New Potent, Enantiomeric SDI, 4–[2–1–R–Hydroxyethyl)–pyrimidin–4–yl]–piperazine–1–sulfonic Acid Dimethylamide.* J. Med Chem, vol. 44, 2001, pp. 2695–2700.
International Search Report dated Jun. 12, 2003.

* cited by examiner

*Primary Examiner*—Venkataraman Balasubramanian
(74) *Attorney, Agent, or Firm*—Edwards & Angell, LLP; Jeffrey D. Hsi

(57) ABSTRACT

This invention features pyrimidine compounds of formula (I):

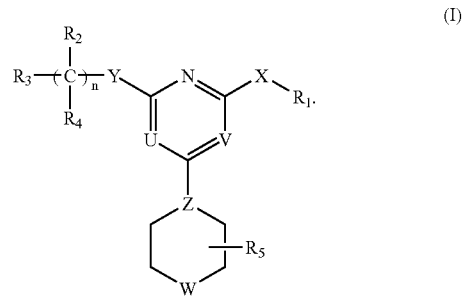

$R_1$ is

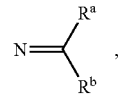

aryl, or heteroaryl; each of $R_2$ and $R_4$, independently, is $R^c$, halogen, nitro, cyano, isothionitro, $SR^c$, or $OR^c$; or $R_2$ and $R_4$, taken together, is carbonyl; $R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; $R_5$ is H or alkyl; n is 0, 1, 2, 3, 4, 5, or 6; X is O, S, S(O), $S(O_2)$, or $NR^c$; Y is a covalent bond, $CH_2$, C(O), C=N—$R^c$, C=N—$OR^c$, C=N—$SR^c$, O, S, S(O), $S(O_2)$, or $NR^c$; Z is N or CH; one of U and V is N, and the other is $CR^c$; and W is O, S, S(O), $S(O_2)$, $NR^c$, or $NC(O)R^c$; in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl.

46 Claims, No Drawings

PYRIMIDINE COMPOUNDS

CROSS REFERENCE TO RELATED APPLICATION

Pursuant to 35 U.S.C. § 120, this application is a continuation prior U.S. application Ser. No. 10/000,742, filed on Nov. 30, 2001 now U.S. Pat. No. 6,693,097. The contents of the prior application is incorporated herein by reference in its entirety.

BACKGROUND

Interleukin-12 (IL-12) is a heterodimeric cytokine (p70) composed of two subunits (p35 and p40), and plays key roles in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Overproduction of IL-12 causes excessive Th1 responses, and may result in inflammatory disorders, such as insulin-dependent diabetes mellitus, multiple sclerosis, rheumatoid arthritis, psoriasis, Crohn's disease, or sepsis. See, for example, Gately et al. (1998) *Annu Rev Immunol.* 16: 495; and Abbas et al. (1996) *Nature* 383: 787. Thus, inhibiting IL-12 overproduction is an approach to treat the just-mentioned diseases. Trembleau et al. (1995) *Immmunol. Today* 16: 383; and Adorini et al. (1997) *Chem. Immunol.* 68: 175. For example, overproduction of IL-12 and the resultant excessive Th1 type responses can be suppressed by modulating IL-12 production. A compound that down-regulates IL-12 production can be used for treating inflammatory diseases. Ma et al. (1998) *Eur Cytokine Netw* 9: 54.

SUMMARY

In one aspect, this invention features pyrimidine compounds of formula (I):

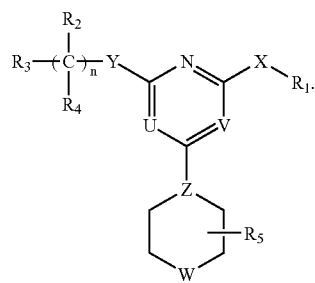

(I)

$R_1$ is

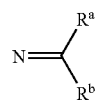

[referred to hereinafter as $NC(R^aR^b)$], aryl, or heteroaryl; each of $R_2$ and $R_4$, independently, is $R^c$, halogen, nitro, cyano, isothionitro, $SR^c$, or $OR^c$; or $R_2$ and $R_4$, taken together, is carbonyl; $R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; $R_5$ is H or alkyl; n is 0, 1, 2, 3, 4, 5, or 6; X is O, S, S(O), S($O_2$), or $NR^c$; Y is a covalent bond, $CH_2$, C(O), C=N—$R^c$, C=N—$OR^c$, C=N—$SR^c$, O, S, S(O), S($O_2$), or $NR^c$; Z is N or CH; one of U and V is N, and the other is $CR^c$; and W is O, S, S(O), S($O_2$), $NR^c$, or $NC(O)R^c$; in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl. Note that the left atom shown in any substituted group described above is closest to the pyrimidine ring. Also note that when n is 2 or greater, the just-described pyrimidine compound may have two or more different $C(R^2R^4)$ moieties. The same rule applies to other similar situations.

Referring to formula (I), a subset of the pyrimidine compounds of this invention is featured by that $R^1$ is $NC(R^aR^b)$. In these compounds, U can be N, V can be CH, Z can be N, and W can be O. In addition, X can be $NR^c$; $R^c$ can be H, methyl, ethyl, or acetyl; Y can be O or $CH_2$, and n can be 0, 1, 2, 3, or 4. In some embodiments, $R_3$ is aryl, heteroaryl (e.g., pyridinyl), $OR^c$, $SR^c$, $C(O)OR^c$, or $C(O)NR^cR^d$. In other embodiments, $R_3$ is

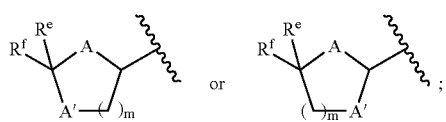

in which each of A and A', independently, is O, S, or NH; each of $R^e$ and $R^f$, independently, is H, alkyl, aryl, or heteroaryl; and m is 1 or 2.

In this subset of pyrimidine compounds, $R^a$ or $R^b$, preferably, is

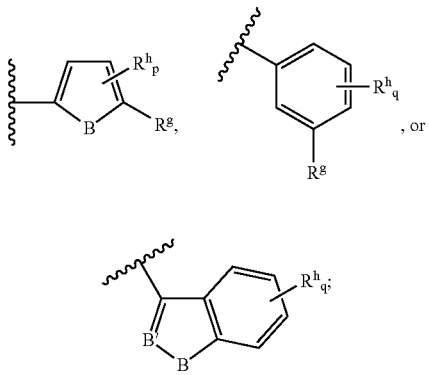

in which B is $NR^i$, O, or S; B' is N or $CR^i$; $R^g$ is H, alkyl, or alkoxyl; $R^h$ is halogen, $NO_2$, CN, alkyl, aryl, heteroaryl, $OR^e$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; $R^i$ is H, alkyl, or alkylcarbonyl; p is 0, 1, or 2; and q is 0, 1, 2, 3, or 4. Preferably, B is $NR^i$; B' is CH; $R^g$ is H, methyl, ethyl, propyl, cyclopropyl, methoxy, or ethoxy; $R^h$ is F, Cl, CN, methyl, methoxy, ethoxy, $OC(O)CH_3$, $OC(O)C_2H_5$, C(O)OH, C(O)$OC_2H_5$, $C(O)NH_2$, $NHC(O)CH_3$, or $S(O_2)NH_2$; $R^i$ is H, methyl, ethyl, or acetyl; and q is 0, 1, or 2.

Another subset of the pyrimidine compounds of this invention is featured by that $R^1$ is aryl or heteroaryl. In these compounds, U can be N, V can be CH, Z can be N, and W can be O. In addition, X can be $NR^c$; $R^c$ can be H, methyl, ethyl, or acetyl; Y can be O or $CH_2$, and n can be 0, 1, 2, 3, or 4. In some embodiments, $R_3$ is aryl, heteroaryl (e.g., pyridinyl), $OR^c$, $SR^c$, $C(O)OR^c$, or $C(O)NR^cR^d$. In other embodiments, $R_3$ is

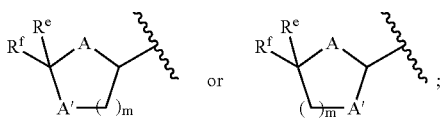

in which each of A and A', independently, is O, S, or NH; each of $R^e$ and $R^f$, independently, is H, alkyl, aryl or heteroaryl; and m is 1 or 2.

In this second subset of pyrimidine compounds, $R_1$, preferably, is

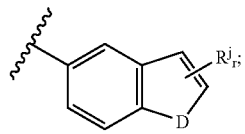

in which D is O, S, or $NR^m$; $R^j$ is benzo, halogen, CN, hydroxyl, alkyl, aryl, heteroaryl, alkoxyl, aryloxyl, or heteroaryloxyl; $R^m$ is H, alkyl, or alkylcarbonyl; and r is 0, 1, or 2. Preferably, $R_1$ is

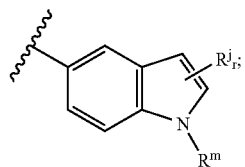

and $R^j$ is methyl, ethyl, propyl, or benzo; and r can be 1 or 2.

Alkyl, alkenyl, alkynyl, aryl, heteroaryl (e.g., pyridinyl), cyclyl, heterocyclyl mentioned above include both substituted and unsubstituted moieties. The term "substituted" refers to one or more substituents (which may be the same or different), each replacing a hydrogen atom. Examples of substituents include, but are not limited to, halogen, hydroxyl, amino, alkylamino, arylamino, dialkylamino, diarylamino, cyano, nitro, mercapto, carbonyl, carbamido, carbamyl, carboxyl, thioureido, thiocyanato, sulfoamido, $C_1 \sim C_6$ alkyl, $C_1 \sim C_6$ alkenyl, $C_1 \sim C_6$ alkoxy, aryl, heteroaryl, cyclyl, heterocyclyl, wherein alkyl, alkenyl, alkoxy, aryl, heteroaryl cyclyl, and heterocyclyl are optionally substituted with $C_1 \sim C_6$ alkyl, aryl, heteroaryl, halogen, hydroxyl, amino, mercapto, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, furyl, fluorenyl, pyrrolyl, thienyl, oxazolyl, imidazolyl, thiazolyl, pyridinyl, pyrimidinyl, quinazolinyl, and indolyl.

Set forth below are exemplary compounds of this invention:

Compound 1:

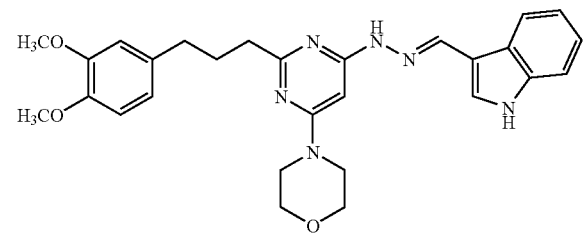

Compound 2:

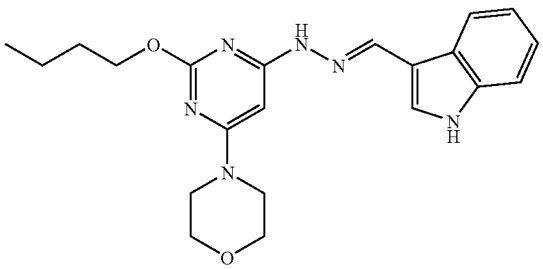

Compound 3:

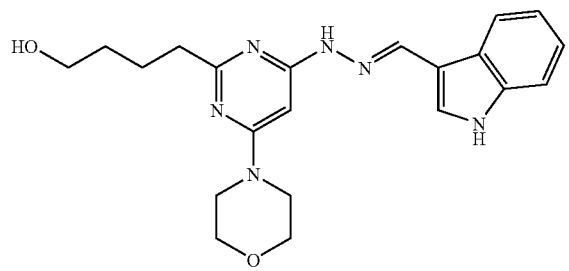

Compound 4:

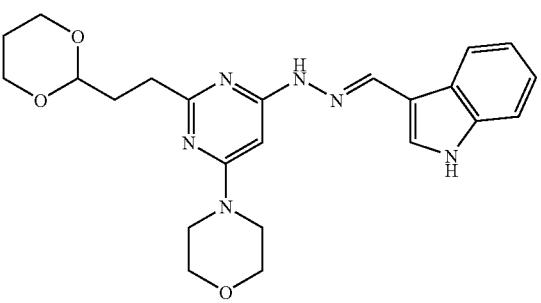

Compound 5:

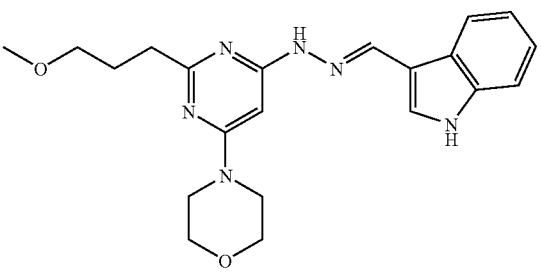

Compound 6:

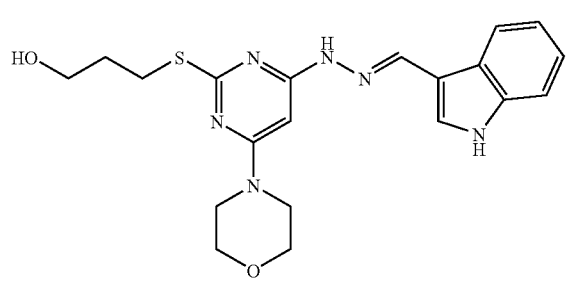

Compound 7:
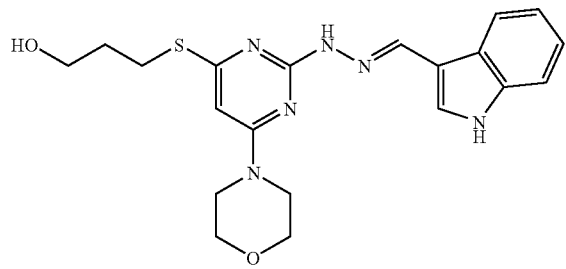
Compound 8:
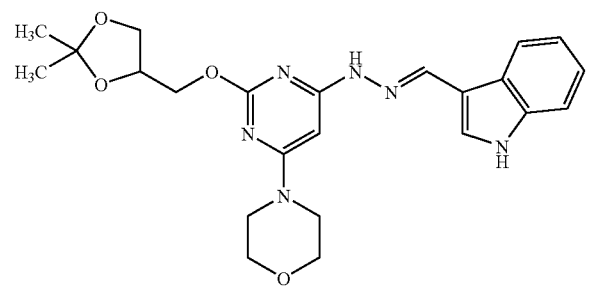
Compound 9:
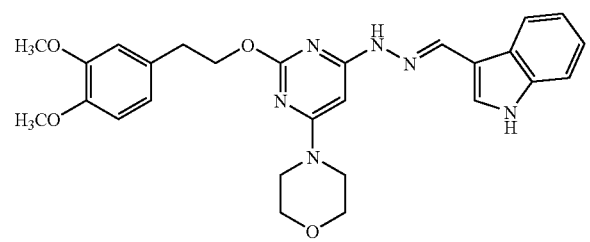
Compound 10:
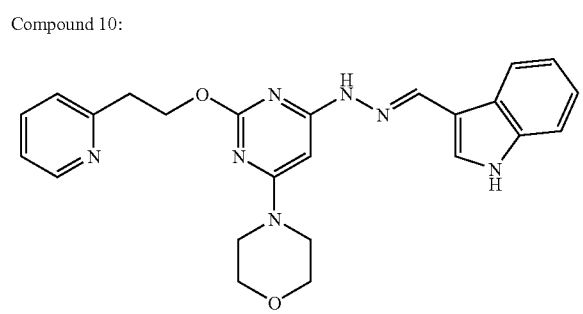
Compound 11:
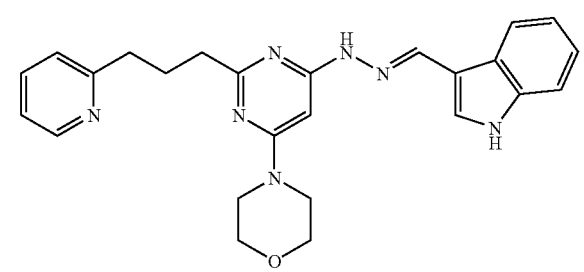
Compound 12:
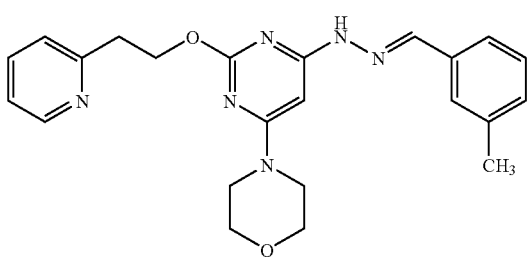
Compound 13:
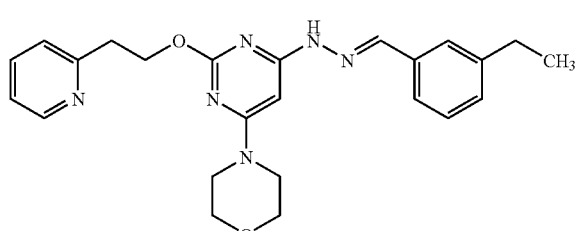
Compound 14:
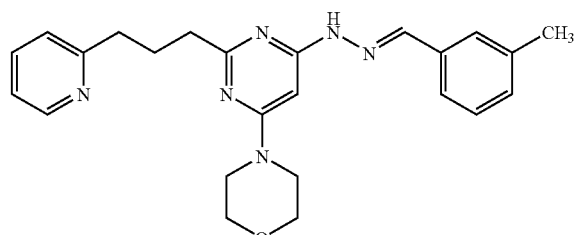
Compound 15:
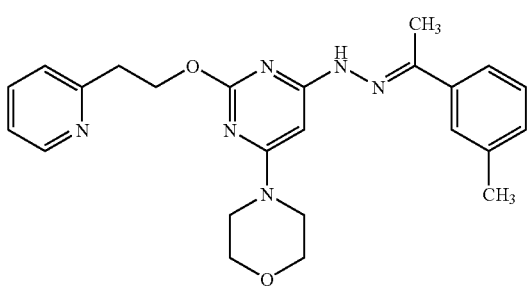
Compound 16:
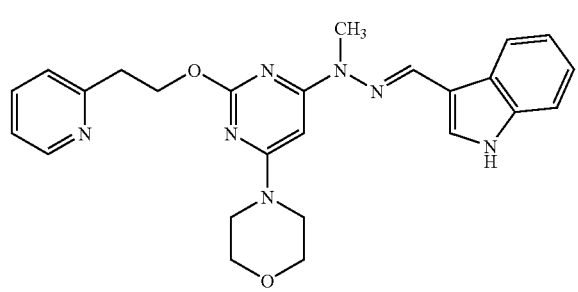

Compound 17:
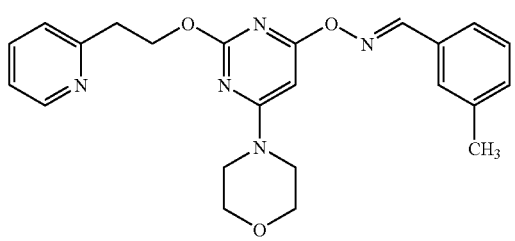
Compound 18:
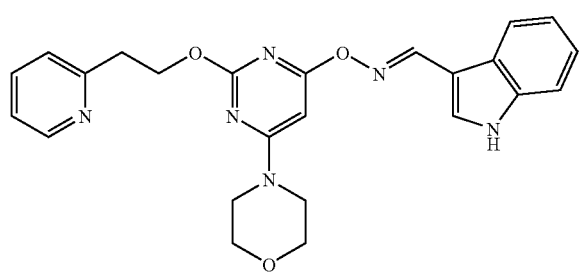
Compound 19:
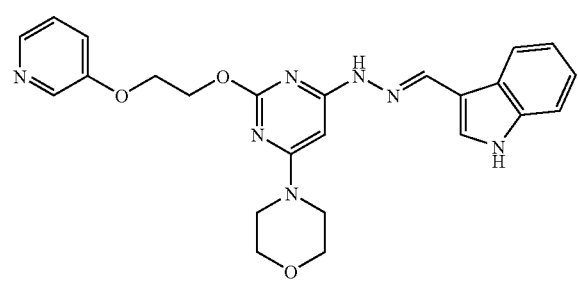
Compound 20:
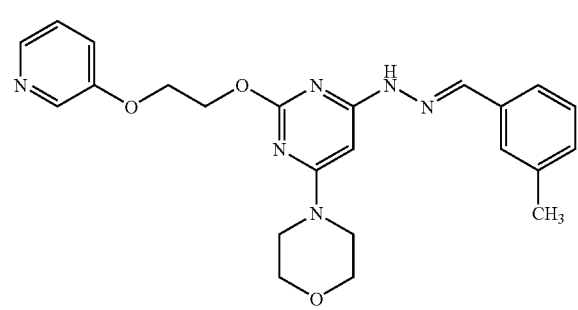
Compound 21:
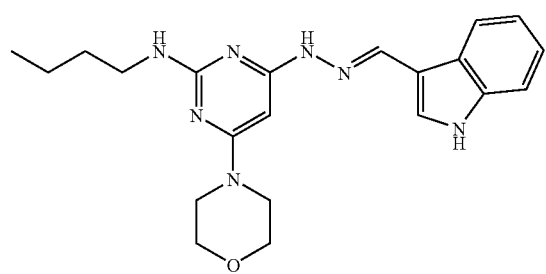
Compound 22:
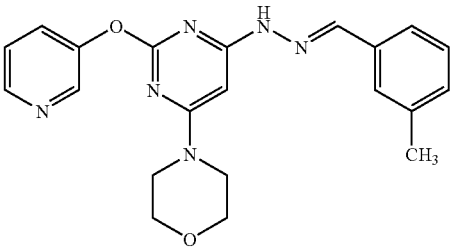
Compound 23:
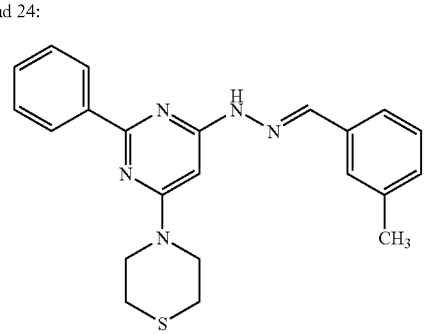
Compound 24:
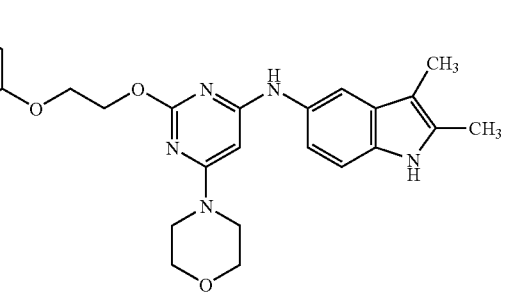
Compound 25:
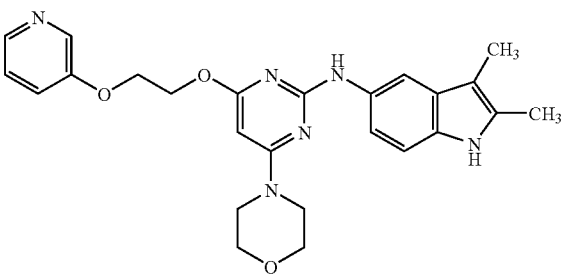
Compound 26:

-continued

Compound 27:

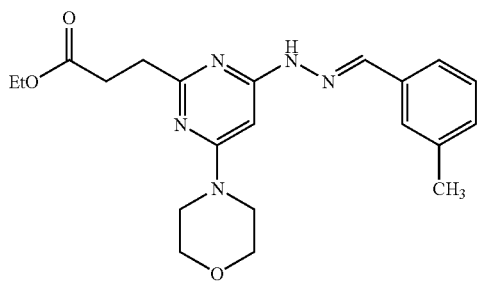

In another aspect, this invention features a pharmaceutical composition that contains a pharmaceutically acceptable carrier and an effective amount of at least one of the pyrimidine compounds of this invention.

In further another aspect, the present invention features a method for treating an IL-12 overproduction-related disorder (e.g., rheumatoid arthritis, sepsis, Crohn's disease, multiple sclerosis, psoriasis, or insulin-dependent diabetes mellitus). The method includes administering to a subject in need thereof an effective amount of one or more pyrimidine compounds of this invention.

The pyrimidine compounds of this invention include the compounds themselves, as well as their salts and their prodrugs, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the pyrimidine compounds described above.

In addition, some of the pyrimidine compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Also within the scope of this invention are a composition containing one or more of the compounds described above for use in treating an IL-12 overproduction-related disorder, and the use of such a composition for the manufacture of a medicament for the just-described use.

The details of one or more embodiments of the invention are set forth in the accompanying drawings and the description below. Other features, objects, and advantages of the invention will be apparent from the description and drawings, and from the claims.

DETAILED DESCRIPTION

The compounds described above can be prepared by methods well known in the art, as well as by the synthetic routes disclosed herein. For example, a pyrimidine compound (e.g., Compounds 1–27) can be prepared by using 2,4,6-trichloro-pyrimidine as a starting material. The three chloro groups can be displaced by various substitutes. More specifically, first chloro group (e.g., at position 6) can react with, e.g., morpholine, to form a morpholinyl pyrimidine.

2-Aryl and 2-alkylpyrimidinde dichloro compounds can also be prepared by reacting an amidine with a malonic ester followed by treatment with phosphorous oxychloride. Second chloro group can be replaced by reacting with a nucleophile, such as an alcohol in the presence of base, e.g., sodium hydride. In other examples, a compound of formula (I), wherein Y is $CH_2$ (e.g., Compound 1), can be prepared by reacting the pyrimidine chloride with a Grignard reagent, an organotin reagent, an organocopper reagent, an organoboric acid, or an organozinc reagent in the presence of an organopalladium compound as a catalyst. Isomeric forms may be produced. The desired isomeric product can be separated from others by, e.g., high performance liquid chromatography. Third chloro group undergoes a displacement reaction with, e.g., hydrazine, and the primary amine of the coupled hydrazine moiety further reacts with an aldehyde, e.g., indole-3-carboxaldehyde to form a hydrazone linkage. Thus, a pyrimidine compound of this invention is obtained. If preferred, other types of linkages can be prepared by similar reactions. Sensitive moieties on a pyrimidinyl intermediate and a nucleophile can be protected prior to coupling. For suitable protecting groups, see, e.g., Greene (1981) *Protective Groups in Organic Synthesis*, John Wiley & Sons, Inc., New York. A pyrimidine compound of this invention can be further purified by flash column chromatography, high performance liquid chromatography, or crystallization.

Also within the scope of this invention is a pharmaceutical composition that contains an effective amount of one or more of the pyrimidine compounds of this invention and a pharmaceutically acceptable carrier. Further, the present invention covers a method of administering an effective amount of such a compound to a subject in need of treatment of IL-12 overproduction related diseases (e.g., rheumatoid arthritis, sepsis, Crohn's disease, multiple sclerosis, psoriasis, or insulin-dependent diabetes mellitus). "An effective amount" refers to the amount of the compound which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the pyrimidine compound of this invention can range from about 0.001 mg/Kg to about 1000 mg/Kg. Effective doses will also vary, as recognized by those skilled in the art, depending on the diseases treated, route of administration, excipient usage, and the possibility of co-usage with other therapeutic treatments such as use of other agents.

To practice the method of the present invention, a pyrimidine compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in- the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A pyrimidine compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the pyrimidine compounds. Examples of other carriers include colloidal silicon dioxide, magnesium stearate, cellulose, sodium lauryl sulfate, and D&C Yellow # 10.

The biological activities of a pyrimidine compound can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A pyrimidine compound can also be evaluated by animal studies. For example, one of such studies involves the ability of a test compound to treat adjuvant arthritis (i.e., a IL-12 overproduction related disorder) in rats.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLE 1

Preparation of Compound 1: N-{2-[3-(3,4-dimethoxy-phenyl)-propyl]-6-morpholin-4-yl-pyrimidin-4-yl}-N'-(1H-indol-3-ylmethylene)-hydrazine To a solution of 3-(3,4-dimethoxyphenyl)-propyl iodide (1.224 g; 4.0 mmol) in 20 mL dry THF, highly active zinc (suspension in THF, Rieke metal from Aldrich, 5.2 mL 0.05 g/mL, 4.0 mmol) was added to obtain a mixture. The mixture was stirred at room temperature overnight. 2,4-dichloro-6-morpholinopyrimidine (0.932 g, 4.0 mmol) and trans-benzyl-(chloro)-bis-(triphenylphosphine)palladium(II) (0.03 g, 0.04 mmol) were added to the mixture, and stirred at 60° C. for 2 days. After routine workup, 4-chloro-2-[3-(3,4-dimethoxyphenyl)propyl]-6-morpholinopyrimidine (0.34 g, 0.90 mmol, 22.4%) was separated from 2-chloro-4-[3-(3,4-dimethoxyphenyl)propyl]-6-morpholinopyrimidine (0.45 g, 1.19 mmol, 30%) by flash chromatography purification.

$^1$H NMR (300 MHz, $CDCl_3$), δ (ppm): 6.70–6.80 (m, 3H); 6.32 (s, 1H); 3.87 (s, 3H); 3.85 (s, 3H); 3.73–3.78 (m, 4H); 3.60–3.64 (m, 4H); 2.76 (d, J=7.8 Hz, 2H); 2.63 (d, J=7.5 Hz, 2H); and 2.01–2.12 (m, 2H).

MS (ESI): m/z 380.2 (M+H).

Further, 4-chloro-2-[3-(3,4-dimethoxyphenyl)propyl]-6-morpholinopyrimidine (0.34 g, 0.90 mmol) was reacted with hydrazine (0.29 g, 9 mmol) to obtain 2-[3-(3,4-dimethoxyphenyl)propyl]-4-hydrazino-6-morpholinopyrimidine as a white solid (0.30 g, 0.80 mmol, 89%).

$^1$H NMR (300 MHz, $CDCl_3$), δ (ppm): 6.73–6.80 (m, 3H); 5.88 (s, 1H); 5.74 (s, 1H); 3.87 (s, 3H); 3.85 (s, 3H); 3.76–3.79 (m, 4H); 3.69 (d, J=0.6 Hz, 2H); 3.56–3.60 (m, 4H); 2.64 (d, J=7.5 Hz, 4H); and 2.00–2.15 (m, 2H).

MS (ESI): m/z 374.2 (M−H).

A 5 mL methanol solution containing 2-[3-(3,4-dimethoxyphenyl)-propyl]-4-hydrazino-6-morpholinopyrimidine (0.177 g, 0.50 mmol), indole-3-carboxaldehyde (0.073 g, 0.50 mmol), and AcOH (20 mg, cat.) was stirred at 70° C. for 4 hours. Solvent was removed and the crude residue was purified using flash chromatography to give Compound 1 as a light brown solid (0.21 g, 0.42 mmol, 84%).

$^1$H NMR (300 MHz, $CDCl_3$), δ (ppm): 8.57 (br s, 1H); 8.45 (br s, 1H); 8.29–8.32 (m, 1H); 8.00 (s, 1H); 7.39–7.43 (m, 2H); 7.23–7.34 (m, 2H); 6.74–6.80 (m, 3H); 6.30 (s, 1H); 3.86 (s, 3H); 3.85 (s, 3H); 3.78–3.84 (m, 4H); 3.67–3.70 (m, 4H); 2.63–2.71 (m, 4H), and 2.03–2.13 (m, 2H).

MS (ESI): m/z 501.2 (M+H).

EXAMPLE 2

Preparation of Compound 2: N-(2-n-butoxy-6-morpholin-4-yl-pyrimidin-4-yl)-N'-(1H-indol-3-ylmethylene)-hydrazine To a solution of 2,4,6-trichloro pyrimidine (25 g, 136 mmol) in $CH_2Cl_2$ (500 mL) at −78° C., morpholine (11.89 mL, 136 mmol) was slowly added, followed by DIPEA (25 mL, 143 mmol). The obtained reaction mixture was stirred at −78° C. for 5 h, and then warmed up to room temperature. The reaction mixture was washed with water. The obtained organic phase was dried over $Na_2SO_4$. The solvent was removed under reduced pressure. The crued residue, 2,4-Dichloro-6-(morpholin-4-yl)pyrimidine, was recrystallized from EtOAc to give white crystals (24.7 g, 77%) 15 g.

$^1$H NMR (300 MHz, $CDCl_3$), δ (ppm): 6.40 (s, 1H); and 4.0–3.5 (m, 8H).

MS (ESI): m/z 234.0 (M+H).

To a solution of n-butanol (0.633 g, 8.54 mmol) in anhydrous DMF (50 mL) at 0° C. under the $N_2$, NaH (0.307 g, 12.8 mmol) was added quickly. The obtained suspension was stirred for 0.5 h at 0° C. 2,4-Dichloro-6-(morpholin-4-yl)pyrimidine (2 g, 8.54 mmol) was added to the suspension. After the suspension was warmed to room temperature and stirred for 12 h, the reaction mixture was quenched with ice/brine and extracted with 200 mL EtOAc. The extract was washed with brine, and dried over $Na_2SO_4$. The solvent was removed under reduced pressure. The crude residue was purified using flash chromatography (silica; EtOAc/Hexane: 1/6) to yield 1.4 g of 2-n-butoxy-4-chloro-6-(morpholin-4-yl)pyrimidine (white solid, 60%).

$^1$H NMR (300 MHz, $CDCl_3$), δ (ppm): 6.20 (s, 1H); 4.26 (t, J=6.6 Hz, 2H); 3.78–3.70 (m, 4H); 3.66–3.56 (m, 4H); 1.80–1.68 (m, 2H); 1.54–1.40 (m, 2H); and 0.96 (t, J=6.9, 3H).

MS (ESI): m/z 272.1 (M+H).

To a solution of 2-n-butoxy-4-chloro-6-(morpholin-4-yl) pyrimidine (1.38 g, 5.1 mmol) in dioxane (50 ml), anhydrous hydrazine (1.6 mL, 50 mmol) was added. The obtained reaction mixture was heated to 95° C., and stirred for 12 h under $N_2$. After cooling to room temperature, the reaction mixture was quenched with ice-brine and extracted with EtOAc (200 mL). The organic extract was washed with brine, water, and dried over $Na_2SO_4$. The solvent was removed under reduced pressure. The crude residue was recrystallized from methanol to obtain 2-n-butoxy-4-hydrazino-6-(morpholin-4-yl)pyrimidine as white crystals (1.10 g, 81%).

$^1$H NMR (300 MHz, $CDCl_3$), δ (ppm): 5.89 (br s, 1H), 5.49 (s, 1H), 4.26 (t, J=6.6, 2H), 3.84–3.78 (m, 6H), 3.62–3.47 (m, 4H), 1.82–1.67 (m, 2H), 1.55–1.42 (m, 2H), and 0.96 (t, J=6.9, 3H);

MS (ESI): m/z 268.2 (M+H).

To a solution of 2-n-butoxy-4-hydrazino-6-(morpholin-4-yl)pyrimidine (200 mg, 0.748 mmol) in MeOH (20 mL), indole-3-carboxaldehyde (108.6 mg, 0.748 mmol) and acetic acid (a drop) were added sequentially. The obtained reaction mixture was stirred at room temperature for 12 h. White precipitate was formed, collected, and washed with 2 mL methanol to give 200 g of Compound 2 (68%).

$^1$H NMR (300 MHz, $CDCl_3$), δ (ppm): 8.36 (br s, 1H), 8.30 (dd, J=6.6, 1.8, 1H), 8.05 (s, 1H), 8.00 (s, 1H), 7.44–7.40 (m, 2H), 7.33–7.24 (m, 2H), 6.13 (s, 1H), 4.26 (t, 2H, J=6.6), 3.84–3.78 (m, 4H), 3.70–3.64 (m, 4H), 1.80–1.70 (m, 2H), 1.54 –1.42 (m, 2H), and 0.96 (t, J=6.9, 3H);

MS (ESI): m/z 395.2 (M+H).

EXAMPLE 3

Preparation of Compound 3: N-(2-(4-hydroxybutyl)-6-morpholin-4-yl-pyrimidin-4-yl)-N'-(1H-indol-3-ylmethylene)-hydrazine A mixture of 4-ethoxy-4-oxo-butylzinc bromide (50 mL 0.5M in THF, 25 mmol), 2,4-dichloro-6-morpholinopyrimidine (4.68 g, 20.0 mmol) and trans-benzyl (chloro)bis(triphenylphosphine)palladium(II) (0.15 g, 0.2 mmol) in THF (total volume 80 mL) was stirred at 60° C. for 2 days. After routine workup, flash chromatography purification was performed to obtain 4-chloro-2-(4-ethoxy-4-oxo-butyl)-6-morpholinopyrimidine as a white solid (2.073 g, 6.60 mmol, 33.0%).

To a solution of 4-chloro-2-(4-ethoxy-4-oxo-butyl)-6-morpholinopyrimidine (1.108 g, 3.54 mmol) in 50 mL THF at −78° C., a diisobutylaluminum hydride (DIBAL) solution (4.72 mL 1.5 M in Toluene, 7.08 mmol) was slowly added. After addition, the obtained reaction mixture was warmed up slowly to 0° C. and kept at 0° C. for 10 min. After routine workup, flash chromatography was performed to obtain 4-chloro-2-(4-hydroxybutyl)-6-morpholinopyrimidine (0.76 g, 2.80 mmol, 79%) as light yellow solid.

$^1$H NMR (300 MHz, $CDCl_3$), δ (ppm): 6.33 (s, 1H), 3.76–3.79 (m, 4H); 3.61–3.68 (m, 6H); 2.76 (t, J=7.8 Hz, 2H); 1.81–1.91 (m, 2H); and 1.60–1.74 (m, 3H).

MS (ESI): m/z 370.2 (M+H).

Following the typical procedure, 4-chloro-2-(4-hydroxybutyl)-6-morpholinopyrimidine (0.542 g, 2.00 mmol, 1.00 equiv.) was reacted with hydrazine and indole-3-carboxaldehyde to give Compound 3 as an off-white solid (0.75 g, 1.90 mmol, 95%).

$^1$H NMR (300 MHz, DMSO-$d_6$), δ (ppm): 11.47 (s, 1H); 10.64 (s, 1H); 8.25 (s, 1H); 8.18 (d, J=6.6 Hz, 1H); 7.71 (s, 1H); 7.43 (d, J=8.4 Hz, 1H); 7.17–7.20 (m, 2H); 6.16 (s, 1H), 4.37 (t, J=4.8 Hz, 1H); 3.72 (br s, 4H); 3.55 (br s, 4H); 3.41–3.45 (m, 2H); 2.49–2.54 (m, 2H), 1.66–1.76 (m 2H); and 1.42–1.53 (m 2H).

MS (ESI): m/z 395.1 (M+H).

EXAMPLE 4

Preparation of Compound 4: N-[2-(2-[1,3]dioxan-2-yl-ethyl)-6-morpholin-4-yl-pyrimidin-4-yl]-N'-(1H-indol-3-ylmethylene)-hydrazine Compound 4 was prepared in a similar manner as described in Example 1.

$^1$H NMR (300 MHz, DMSO-$d_6$), δ (ppm): 11.46 (s, 1H); 10.64 (s, 1H); 8.25 (s, 1H); 8.18 (d, J=6.6 Hz, 1H); 7.71 (s, 1H); 7.43 (d, J=6.0 Hz, 7.5 Hz, 1H); 7.16–7.19 (m, 2H); 6.15 (s, 1H), 4.58 (t, J=5.1 Hz, 1H); 4.00 (dd, J=11.4 Hz, 4.5 Hz, 2H); 3.64–3.72 (m, 6H); 3.54 (br s, 4H); 2.50–2.59 (m, 2H); 1.80–1.94 (m, 3H), and 1.33 (d, J=9.6 Hz, 1H).

MS (ESI): m/z 437.2 (M+H).

EXAMPLE 5

Preparation of Compound 5: N-(1H-indol-3-ylmethylene)-N'-[2-(3-methoxy-propyl)-6-morpholin-4-yl-pyrimidin-4-yl]-hydrazine Following the procedure for the synthesis of N-(2-(4-Hydroxybutyl)-6-morpholin-4-yl-pyrimidin-4-yl)-N'-(1H-indol-3-ylmethylene)-hydrazine (Compound 3), 4-chloro-2-(3-hydroxypropyl)-6-morpholinopyrimidine (0.81 g, 3.15 mmol) was synthesized, methylated with sodium hydride (0.48 g, 6.30 mmol) for 10 min, and MeI (0.895 g, 6.30 mmol) for 5 h in 30 mL THF at 0° C. to give 4-chloro-2-(3-methoxypropyl)-6-morpholinopyrimidine as colorless viscous oil (0.792 g, 3.03 mmol, 96%).

¹H NMR (300 MHz, CDCl₃), δ (ppm): 6.32 (s, 1H), 3.75–3.79 (m, 4H); 3.61–3.64 (m, 4H); 3.44 (t, J=6.6 Hz, 2H); 3.34 (s, 3H); 2.78 (t, J=7.8 Hz, 2H); and 2.00–2.09 (m, 2H).

MS (ESI): m/z 262.1 (M+H).

Following the typical procedure, 4-chloro-2-(3-methoxypropyl)-6-morpholinopyrimidine (0.783 g, 3.00 mmol) was treated with hydrazine and indole-3-carboxaldehyde sequentially to yield 0.89 g of Compound 5 (2.26 mmol, 75%).

¹H NMR (300 MHz, DMSO-d₆), δ (ppm): 11.46 (s, 1H); 10.64 (s, 1H); 8.26 (s, 1H); 8.17–8.20 (m, 1H); 7.72 (d, J=2.4 Hz, 1H); 7.43 (dd, J=6.0 Hz, 2.4 Hz, 1H); 7.15–7.21 (m, 2H); 6.16 (s, 1H); 3.70–3.73 (m, 4H); 3.52–3.56 (m, 4H); 3.37 (t, J=6.9 Hz, 2H); 3.23 (s, 3H); 2.50–2.57 (m, 2H), and 1.88–1.97 (m, 2H).

MS (ESI): m/z 395.2 (M+H).

EXAMPLE 6

Preparation of Compound 6: 3-{4-[N'-(1H-indol-3-ylmethylene)-hydrazino]-6-morpholin-4-yl-pyrimidin-2-ylsulfanyl}-propan-1-ol Compound 6 was prepared in a similar manner as described in Example 2.

¹H NMR (300 MHz, DMSO-d₆), δ (ppm): 11.48 (s, 1H); 10.68 (s, 1H); 8.26 (s, 1H); 8.15–8.18 (m, 1H); 7.73 (d, J=2.1 Hz, 1H); 7.42–7.44 (m, 1H); 7.16–7.20 (m, 2H); 6.04 (s, 1H), 4.53 (t, J=5.1 Hz, 1H); 3.65–3.71 (m, 4H); 3.48–3.56 (m, 6H); 3.06 (t, J=7.2 Hz, 2H), and 1.76–1.85 (m, 2H).

MS (ESI): m/z 413.1 (M+H).

EXAMPLE 7

Preparation of Compound 7: 3-{2-[N'-(1H-indol-3-ylmethylene)-hydrazino]-6-morpholin-4-yl-pyrimidin-4-ylsulfanyl}-propan-1-ol Compound 7 was prepared in a similar manner as described in Example 2.

¹H NMR (300 MHz, DMSO-d₆), δ (ppm): 11.34 (s, 1H); 10.48 (s, 1H); 8.45 (d, J=7.8 Hz, 1H); 8.25 (s, 1H); 7.64 (d, J=2.7 Hz, 1H); 7.40 (d, J=8.1 Hz, 1H); 7.05–7.19 (m, 2H); 6.08 (s, 1H), 4.60 (t, J=5.1 Hz, 1H); 3.50–3.68 (m, 10H); 3.20–3.30 (m, 2H); and 1.78–1.86 (m, 2H).

MS (ESI): m/z 413.1 (M+H).

EXAMPLE 8

Preparation of Compound 8: N-[2-(2,2-dimethyl-[1,3]dioxolan-4-ylmethoxy-6-morpholin-4-yl-pyrimidin-4-yl]-N'-(1H-indol-3-ylmethylene)-hydrazine Compound 8 was prepared in a similar manner as described in Example 2.

¹H NMR (300 MHz, CDCl₃), δ (ppm): 8.38 (br s, 1H); 8.30 (dd, J=7.2, 1.8, 1H), 8.02 (br s, 1H); 8.00 (s, 1H); 7.44–7.41 (m, 2H); 7.32–7.26 (m, 2H); 6.14 (s, 1H); 4.51–4.42 (m, 2H); 4.22–4.12 (m, 2H); 3.96–3.91 (m, 1H); 3.84–3.79 (m, 4H); 3.70–3.64 (m, 4H); 1.47 (s, 3H); and 1.38(s, 3H).

MS (ESI): m/z 453.2 (M+H).

EXAMPLE 9

Preparation of Compound 9: N-{2-[2-(3,4-dimethoxy-phenyl)-ethoxy]-6-morpholin-4-yl-pyrimidin-4-yl}-N'-(1H-indol-3-ylmethylene)-hydrazine Compound 9 was prepared in a similar manner as described in Example 2.

¹H NMR (300 MHz, CDCl₃), δ (ppm): 8.43 (bs, 1H); 8.30 (d, J=7.5 Hz 1H); 8.2 (bs, 1H); 8.02 (d, J=2.7 Hz, 1H); 7.46–7.40 (m, 2H); 7.30–7.26 (m, 2H); 6.82 (d, J=1 Hz, 3H); 4.45 (d, J=3.6 Hz, 1H); 4.45 (t, J=5.2 Hz, 2H); 3.87 (d, J=3.9 Hz, 3H); 3.86 (d, J=3.9 Hz, 3H); 3.81 (s, 4H); 3.67(s, 4H); and 3.04 (t, J=5.0 Hz, 2H).

MS (ESI): m/z 503.2 (M+H).

EXAMPLE 10

Preparation of Compound 10: N-(1H-indol-3-ylmethylene)-N'-[6-morpholin-4-yl-2-(2-pyridin-2-yl-ethoxy)-pyrimidin-4-yl]-hydrazine Compound 10 was prepared in a similar manner as described in Example 2.

¹H NMR (300 MHz, CDCl₃), δ (ppm): 9.3 (bs, 1H); 8.66 (s, 1H); 8.55–8.53 (m, 1H); 8.28–8.26 (m, 1H); 8.04 (s, 1H); 7.62–7.57 (m, 1H); 7.41–7.10 (m, 6H); 6.08 (s, 1H); 4.64 (t, J=6.6 Hz, 2H); 3.76 (s, 4H); 3.62 (s, 4H); and 3.26 (t, J=6.6 Hz, 2H).

MS (ESI): m/z 444.2 (M+H).

EXAMPLE 11

Preparation of Compound 11: N-(1H-indol-3-ylmethylene)-N'-[6-morpholin-4-yl-2-(3-pyridin-2-propyl)-pyrimidin-4-yl]-hydrazine Compound 11 was prepared in a similar manner as described in Example 1.

¹H NMR (300 MHz, DMSO-d₆), δ (ppm): 11.47 (s, 1H); 10.65 (s, 1H); 8.50(d, J=4.5 Hz, 1H); 8.26 (s, 1H); 8.20–8.18 (m, 1H); 7.72–7.68 (m, 2H); 7.45–7.42 (m, 1H); 7.29–7.18 (m, 4H); 6.17(s, 1H); 3.73 (s, 4H); 3.5 (s, 4H); 2.79 (t, J=7.5 Hz, 2H); 2–58–2.51 (m, 2H); and 2.18–2.06 (m, 2H).

MS (ESI): m/z 442.2 (M+H).

EXAMPLE 12

Preparation of Compound 12: N-(3-methyl-benzylidene)-N'-[6-morpholin-4-yl-2-(2-pyridin-2-yl-ethoxy)-pyrimidin-4-yl]-hydrazine Compound 12 was prepared in a similar manner as described in Example 2.

¹H NMR (300 MHz, CDCl₃), δ (ppm): 8.55–8.48 (m, 2H); 7.71 (s, 1H); 7.65–7.55 (m, 1H); 7.49–7.42 (m, 2H); 7.30–7.15 (m, 4H); 6.08 (s, 1H); 4.64 (t, J=6.6 Hz, 2H); 3.81–3.75 (m, 4H); 3.64–3.61 (m, 4H); 3.25 (t, J=7.0 Hz, 2H); and 2.38 (s, 3H).

MS (ESI): m/z 419.2 (M+H).

EXAMPLE 13

Preparation of Compound 13: N-(3-ethyl-benzylidene)-N'-[6-morpholin-4-yl-2-(2-pyridin-2-yl-ethoxy)-pyrimidin-4-yl]-hydrazine Compound 13 was prepared in a similar manner as described in Example 2.

¹H NMR (300 MHz, CDCl₃), δ (ppm): 8.58–8.50 (m, 1H); 8.43 (s, 1H); 7.95 (s, 1H); 7.64–7.58 (m, 2H);

7.30–7.25 (m, 1H); 7.18–7.05 (m, 3H); 6.07(s, 1H); 4.65 (t, J=6.9 Hz, 2H); 3.80–3.76 (m, 4H); 3.64–3.61 (m, 4H); 3.26 (t, J=6.9 Hz, 2H); 2.40 (q, J=7.6 Hz, 2H); and 1.45 (t, J=7.6 Hz, 3H).

MS (ESI): m/z 433.3 (M+H).

EXAMPLE 14

Preparation of Compound 14: N-(3-methyl-benzylidene)-N'-[6-morpholin-4-yl-2-(3-pyridin-2-yl-propyl)-pyrimidin-4-yl]-hydrazine Compound 14 was prepared in a similar manner as described in Example 1.

$^1$H NMR (300 MHz, CDCl$_3$), δ (ppm): 9.6 (bs, 1H); 8.53 (d, J=4.5 Hz, 1H); 7.76 (s, 1H); 7.56 (t, J=6 Hz, 1H); 7.49–7.47 (m, 2H); 7.28 (m, 1H); 7.18–7.06 (m, 3H); 6.26 (s, 1H); 3.81–3.79 (m, 4H); 3.69–3.67 (m, 4H); 2.89 (t, J=7.8 Hz, 2H); 2.71 (t, J=7.5 Hz, 2H); 2.39 (s, 3H); and 2.22 (t, J=7.5 Hz, 2H).

MS (ESI): m/z 417.2 (M+H).

EXAMPLE 15

Preparation of Compound 15: N-[6-morpholin-4-yl-2-(2-pyridin-2-yl-ethoxy)-pyrimidin-4-yl]-N'-(1-m-tolyl-ethylidene)-hydrazine Compound 15 was prepared in a similar manner as described in Example 2.

$^1$H NMR (300 MHz, CDCl$_3$), δ (ppm): 8.56 (bs, 1H), 7.66–7.46 (m, 4H), 7.32–7.26 (m, 2H), 7.16–7.14 (m, 2H), 6.44(s, 1H), 4.69 (t, J=6.9 Hz, 2H), 3.80–3.77 (m, 4H), 3.63–3.60 (m, 4H), 3.31 (t, J=6.9 Hz, 2H), 2.39 (s, 3H).

MS (ESI): m/z 433.2 (M+H).

EXAMPLE 16

Preparation of Compound 16: N-[1-(1H-indol-3-yl)-ethylidene]-N'-[6-morpholin-4-yl-2-(2-pyridin-2-yl-ethoxy)-pyrimidin-4-yl]-hydrazine Compound 16 was prepared in a similar manner as described in Example 2.

$^1$H NMR (300 MHz, CDCl$_3$), δ (ppm): 9.35 (bs, 1H); 8.54 (dd, J=0.9, 4.2 Hz, 1H); 8.33 (d, J=7.5 Hz, 1H); 7.93 (s, 1H); 7.58 (t, J=7.2 Hz, 1H); 7.36–7.33 (m, 2H); 7.27–7.120 (m, 4H); 6.49 (s, 1H); 4.68(t, J=7.2 Hz, 2H); 3.76–3.73 (m, 4H); 3.60–3–57 (m, 4H); 3.50 (s, 3H); and 3.33–3.28 (t, J=7.0 Hz, 2H).

MS (ESI): m/z 458.2 (M+H).

EXAMPLE 17

Preparation of Compound 17: 3-Methyl-benzaldehyde O-[6-morpholin-4-yl-2-(2-pyridin-2-yl-ethoxy)-pyrimidin-4-yl]-oxime Compound 17 was prepared in a similar manner as described in Example 2.

$^1$H NMR (300 MHz, CDCl$_3$), δ (ppm): 8.56–8.53 (m, 1H); 8.45 (s, 1H); 7.62–7.50 (m, 3H); 7.38–7.26 (m, 3H); 7.18–7.10 (m, 1H); 6.17 (s, 1H); 4.68 (t, J=6.9 Hz, 2H); 3.80–3.76 (m, 4H); 3.67–3.64 (m, 4H); 3.29 (t, J=6.9 Hz, 2H); and 2.41 (s, 3H).

MS (ESI): m/z 420.1 (M+H).

EXAMPLE 18

Preparation of Compound 18: 1H-indole-3-carbaldehyde O-[6-morpholin-4-yl-2-(2-pyridin-2-yl-ethoxy)-pyrimidin-4-yl]-oxime Compound 18 was prepared in a similar manner as described in Example 2.

$^1$H NMR (300 MHz, DMSO-d$_6$), δ (ppm): 11.82 (bs, 1H); 8.81 (s, 1H); 8.50 (d, J=4.5 Hz, 1H); 8.04 (d, J=6.9 Hz, 1H); 7.93(s, 1H); 7.72 (t, J=6.9 Hz, 1H); 7.49 (d, J=6.9 Hz, 1H); 7.33 (d, J=7.8 Hz, 1H); 7.30–7.18 (m, 3H); 6.22 (s, 1H); 4.57 (t, J=6.3 Hz, 2H); 3.67 (s, 4H); 3.56 (s, 4H); and 3.15 (t, J=6.3 Hz, 2H).

MS (ESI): m/z 445.2 (M+H).

EXAMPLE 19

Preparation of Compound 19: N-(1H-indol-3-ylmethylene)-N'-{6-morpholin-4-yl-2-[2-(pyridin-3-yloxy)-ethoxy]-pyrimidin-4-yl}-hydrazine Compound 19 was prepared in a similar manner as described in Example 2.

$^1$H NMR: (300 MHz, CDCl$_3$), δ (ppm): 9.20 (br s, 1H); 8.30 (br s, 1H); 8.29 (t, J=3.3 Hz, 1H); 8.18–8.12 (m, 2H); 7.44–7.41 (m, 2H); 7.26–7.18 (m, 5H); 6.08 (s, 1H); 4.66 (t, J=4.8 Hz, 2H); 4.29 (t, J=5.0 Hz, 2H); 3.80–3.76 (m, 4H); and 3.67–3.62 (m, 4H).

MS (ESI): m/z 460.2 (M+H).

EXAMPLE 20

Preparation of Compound 20: N-(3-methyl-benzylidene)-N'-{6-morpholin-4-yl-2-[2-(pyridin-3-yloxy)-ethoxy]-pyrimidin-4-yl}-hydrazine Compound 20 was prepared in a similar manner as described in Example 2.

$^1$H NMR (300 MHz, CDCl$_3$), δ (ppm): 8.55 (s, 1H); 8.34 (br s, 1H); 8.30–8.23 (m, 1H); 7.78 (s, 1H); 7.50–7.47 (m, 2H); 7.32–7.24 (m, 1H); 7.20–7.17 (m, 3H); 6.14 (s, 1H); 4.66 (t, J=5.0 Hz, 2H); 4.35 (t, J=4.8 Hz, 2H); 3.83–3.80 (m, 4H); 3.68–3.65 (m, 4H); and 2.40(s, 3H).

MS (ESI): m/z 435.2 (M+H).

EXAMPLE 21

Preparation of Compound 21: Butyl-{4-[N'-(1H-indol-3-ylmethylene)-hydrazino]-6-morpholin-4-yl-pyrimidin-2-yl}-amine Compound 21 was prepared in a similar manner as described in Example 2.

$^1$H NMR (300 MHz, CDCl$_3$), δ ppm: 8.41 (bs, 1H), 8.33–8.30 (m, 1H), 8.19 (bs, 1H), 7.95 (s, 1H), 7.41–7.37 (m, 2H), 7.29–7.25 (m, 2H), 5.96 (s, 1H), 4.65 (t, J=4 Hz, 1H), 3.83–3.80 (m, 4H), 3.65–3.62 (m, 4H), 3.36 (dd, J=6.3, 13.5 Hz, 2H), 1.60–1.55 (m, 2H), 1.35–1.33 (m, 4H), 0.92–0.87 (m, 3H).

MS (ESI): m/z 408.2 (M+H).

EXAMPLE 22

Preparation of Compound 22: N-(3-Methyl-benzylidene)-N'-[6-morpholin-4-yl-2-(pyridin-3-yloxy)-pyrimidin-4-yl]-hydrazine To a solution of 3-hydroxypyridine (950 mg, 10 mmol) in anhydrous THF (50 mL) at 0° C. under the nitrogen protection was added NaH (60% in oil) (480 mg, 12 mmol). The suspension was stirred for 0.5 h at 0° C., and 2,4,6-trichloropyrimidine (1.84 g, 10 mmol) was added. After the mixture warmed to room temperature and stirred for 2 h, the reaction was quenched by ice brine and extracted with EtOAc (300 mL). The organic phase was washed with brine, dried (Na$_2$SO$_4$), filtered, evaporated in vacuo. The cure product was purified by flash chromatography on a column of silica gel (EtOAc-Hexane, 1:7). The product (1.80 g, 7.4 mmol) in CH$_2$Cl$_2$ (150 mL) at 0° C. was added slowly morpholine (2.5 g, 28 mmol). The reaction mixture was stirred at 0° C. for 1 h and another 1 h at room temperature. The mixture was washed with water. The organic phase was dried (Na$_2$SO$_4$), filtered and evaporated in vacuo and presented three isomers. The isomers was separated by flash chromatography on a column of silica gel (EtOAc-Hexane, 1:7 and 1:3) to obtain 4-[6-chloro-2-(pyridin-3-yloxy)-pyrimidin-4-yl]-morpholine (320 mg, 14.7%).

$^1$H NMR (300 MHz, CDCl$_3$), δ (ppm): 8.51(d, 1H, J=2.7 Hz), 8.44(dd, 1H, J=1.5, J=3.3 Hz), 7.53–7.49(m, 1H), 7.34–7.3 (m, 1H), 6.25 (s, 1H), 3.71–3.67(m, 4H), 3.51–3.84 (m, 4H).

MS (ESI): m/z 293.1.

To a solution of 4-[6-chloro-2-(pyridin-3-yloxy)-pyrimidin-4-yl]-morpholine (295 mg, 1 mmol) in THF (10 mL) was added anhydrous hydrazine (0,320 ml, 10 mmol) under the nitrogen protection. The mixture was heated at 70° C. for 15 min. After cooling to room temperature, the reaction mixture was quenched by ice brine and extracted with EtOAc (100 mL). The organic phase was washed with brine (10 mL) and water (10 ml×2), dried (Na$_2$SO$_4$), filtered, evaporated, and purified by flash chromatography on a column of silica gel (CH$_2$Cl$_2$ and CH$_2$Cl$_2$-MeOH, 95:5) and to give [6-morpholin-4-yl-2-(pyridin-3-yloxy)-pyrimidin-4-yl]-hydrazine (180 mg) in 62% yield. M/Z (M+1) 289.2

To a solution of [6-morpholin-4-yl-2-(pyridin-3-yloxy)-pyrimidin-4-yl]-hydrazine (180 mg) (145 mg, 0.5 mmol) and m-tolylaldehyde (72 mg, 0.6 mmol) in MeOH (10 mL) was added acetic acid (1 drop). The reaction mixture was stirred at room temperature for 12 h and white solid was precipitated. The resulting precipitate was collected by filtration and washed with little amount of metanol and to give 125 mg of Compound 22 in 64% yield.

$^1$H NMR (300 MHz, CDCl$_3$), δ (ppm): 8.71(s, 1H), 8.57(d, 1H, J=2.4 Hz), 8.44(dd, 1H, J=1.5, 3.2 Hz), 7.78(s, 1H), 7.56–7.52(m, 1H), 7.46–7.43(m, 2H), 7.34–7.26 (m, 2H), 7.17(d, 1H, J=8.1 Hz), 6.17 (s, 1H), 3.76–3.73(m, 4H), 3.57–3.54(m, 4H), 2.38(s, 3H).

MS (ESI): m/z 391.2.

EXAMPLE 23

Preparation of Compound 23: N-(3-Methylbenzlidene)-N'-(5-methyl-6-morpholin-4-yl-2-phenylpyrimidin-4-yl)hydrazine Benzamidine hydrochloride (7.06 g, 0.045 mol) and dimethyl methylmalonate (6.0 g, 0.041 mol) were dissolved in methanol (100 mL). Sodium methoxide (21.5 mL, 0.099 mol, 25 wt % solution in methanol) was added and the solution was stirred at room temperature for 18 h. The volume of solvent was reduced to approximately 50 mL under reduced pressure, then poured onto ice water. This solution was neutralized with HOAc which produced a white precipitate. This precipitate was collected and dried to produce a white solid (6.1 g, 74%).

$^1$H NMR (DMSO-d$_6$) δ (ppm)1.68 (s, 3H), 7.70–7.87 (m, 3H), 8.21 (d, J=8.4 Hz).

MS (ESI): m/z 203.1 (M+H)$^+$

5-Methyl-2-phenyl-pyrimidine-4,6-diol (3.3 g, 0.016 mol) and POCl$_3$ were heated to 60C for 3 hrs. The solution was allowed to cool to room temperature then poured onto ice. The resultant white precipitate was filtered and dried to produce the desired compound as a white solid (810 mg, 21%). $^1$H NMR (DMSO-d$_6$) δ (ppm) 2.40 (s, 3H), 7.51–7.56 (m, 3H), 8.23 (d, 8.4 Hz).

MS (ESI): m/z 239.1 (M+H)$^+$ 4,6-Dichloro-5-methyl-2-phenylpyrimidine (2.5 g, 0.010 mol) and morpholine (2.93 g, 0.031 mol) were dissolved in THF (50 mL) and heated to reflux for 3 hrs. The solution was allowed to cool then EtOAc (100 mL) and water (100 mL) were added. The EtOAc layer was washed with water (3×100 mL), dried over MgSO$_4$, filtered and solvent was removed under reduced pressure. The resultant solid was used without further purification (2.66 g, 92%).

MS (ESI): m/z 298.1 (M+H)$^+$ 4-(6-Chloro-5-methyl-2-phenylpyrimidin-4-yl) morpholine (439 mg, 1.51 mmol) was dissolved in THF (50 mL). Hydrazine (0.25 mL, 7.96 mmol) was added and the solution was heated to reflux for 18 hrs. The reaction was allowed to cool the solvent was removed under reduced pressure. EtOAc (100 mL) and water (100 mL) were added. The EtOAc layer was washed with water (3×100 mL), dried over MgSO$_4$, filtered and solvent was removed under reduced pressure to produce a white solid (374 mg). This solid was redissolved in THF (50 mL) and m-tolualdehyde (157 mg, 1.31 mmol) was added. The solution was heated to reflux for 4 hrs then allowed to cool. Solvent was removed under reduced pressure then EtOAc (100 mL) and water (100 mL) were added. The EtOAc layer was washed with water (3×100 mL), dried over MgSO$_4$, filtered and solvent was removed under reduced pressure. The crude product was purified by silcagel column chromatography, eluting with 25% EtOAc/hexane to produce the pure desired product as a yellow solid (313 mg, 53%). $^1$H NMR (DMSO-d$_6$) δ (ppm) 2.26 (s, 3H), 2.36 (s, 3H), 3.35 (m, 4H), 3.75–3.78 (m, 4H), 7.20 (d, J=6.9 Hz), 7.33 (t, J=6.9 Hz), 7.47–7.52 (m, 5H), 8.19 (s, 1H), 8.35–8.38 (m, 2H), 10.60 (s, 1H).

MS (ESI): m/z 388.3 (M+H)$^+$

EXAMPLE 24

Preparation of Compound 24: N-(3-methyl-benzylidene)-N'-(2-phenyl-6-thiomorpholin-4-yl-pyrimidin-4-yl)-hydrazine Compound 24 was prepared in a similar manner as described in Example 23.

$^1$H-NMR (DMSO-d$_6$) δ 2.36 (s, 3H), 2.76 (s, 4H), 4.07 (s, 4H), 6.36 (s, 1H), 7.19 (d, J=8.1 Hz), 7.32 (t, J=8.1 Hz), 7.47–7.57 (m, 5H), 8.09 (s, 1H), 8.30–8.31 (m, 1H), 11.02 (s, 1H).

MS (ESI): m/z 389.1.

EXAMPLE 25

Preparation of Compound 25: (2,3-Dimethyl-1H-indole-5-yl)-{6-morpholin-4-yl-2-[2-(pyridin-3-yloxy)-ethoxy]-pyrimidin-4-yl}-amine To a solution of 2-(pyridin-3-yloxy)-ethanol (3.48 g, 25 mmol) in 40 mL of anhydrous THF at room temperature under the N$_2$, 2,4,6-trichloro pyrimidine (4.56 g, 25 mmol) was added followed by portionwise addition of NaH (60% suspension in oil, 1.1 g, 27.5 mmol). After 30 min of stirring reaction was quenched with water, water layer extracted with EtOAc, combined organic solutions washed with brine and dried over MgSO$_4$.

Purification using flash chromatography (silica; dichloromethane/acetone/methanol: 3/1/0.1) afforded mixture of 4,6-dichloro-2- and 2,6-dichloro-4-[2-(pyridin-3-yloxy)-ethoxy]-pyrimidines (3.72 g, 52%), (NMR ratio 1:1.2) as an oil.

To a solution of the above mixture (3.72 g, 13 mmol) in 20 mL of 1,4-dioxane was added DIPEA (2.49 mL, 14.3 mmol), followed by 2,3-dimethyl-5-amino-indole (2.08 g, 13 mmol) and a mixture was refluxed for 1 hour. Solvent was removed under reduced pressure and reaction mixture was separated using column chromatography (silica; dichloromethane/acetone/methanol: 3/1/0.1) to afford {6-chloro-2-[2-(pyridin-3-yloxy)-ethoxy]-pyrimidin-4yl}-amine (2.07 g, 39%). An mixture of {4-chloro-6-[2-(pyridin-3-yloxy)-ethoxy]-pyrimidin-4-yl}-amine and {2-chloro-6-[2-(pyridin-3-yloxy)-ethoxy]-pyrimidin-4-yl}-amine (2.5 g, 47%) was also obtained and used in another reaction.

A solution of {6-chloro-2-[2-(pyridin-3-yloxy)-ethoxy]-pyrimidin-4-yl}-amine (2.07 g, 5.05 mmol) and morpholine (1.32 mL, 15.15 mmol) in 1,4-dioxane was heated at 110° C. for 24 hours. Solvent was removed under reduced pressure and reaction mixture was purified using flash chromatography (silica; dichloromethane/acetone/methanol: 3/1/0.1) to afford Compound 25 (2 g, 86%) as a colorless solid.

$^1$H NMR (300 MHz, CDCl$_3$), δ (ppm): 8.34 (br s, 1H), 8.23 (dd, 1H, J=3.6,2.1), 7.96 (brs, 1H), 7.34–7.21 (m, 4H), 6.98(dd, 1H, J=8.4, 1.8 Hz), 6.60 (brs, 1H), 5.36 (s, 1H), 4.65 (t, 2H, J=5.1 Hz), 4.34 (t, 2H, J=5.1 Hz), 3.66 (m, 4H), 3.42 (m, 4H), 2.37(s, 3H), and 2.20 (s, 3H).

MS (ESI): m/z 461.5 (M+H).

EXAMPLE 26

Preparation of Compound 26: (2,3-Dimethyl-1H-indol-5-yl)-{4-morpholin-4-yl-6-[2-(pyridin-3-yloxy)-ethoxy]-pyrimidin-2-yl}-amine Reaction of a mixture of {4-chloro-6-[2-(pyridin-3-yloxy)-ethoxy]-pyrimidin-4-yl}-amine and {2-chloro-6-[2-(pyridin-3-yloxy)-ethoxy]-pyrimidin-4-yl}-amine (2.5 g, 47%) and (2.5 g, 6.1 mmol) with morpholine was carried out as described in Example 24.

Purification by flash chromatography and recrystallization from ether-pentane gave 0.3 g of Compound 26.

$^1$H NMR (300 MHz, CDCl$_3$), δ (ppm): 8.36 (br s, 1H), 8.24 (m, 1H), 7.85 (m, 1H), 7.70 (brs, 1H), 7.26–7.14 (m, 4H), 6.78 (brs, 1H), 5.42 (s, 1H), 4.68 (t, 2H, J=5.1), 4.31 (t, 2H, J=5.1), 3.70 (m, 4H), 3.54 (m, 4H), 2.35(s, 3H), and 2.18 (s, 3H).

MS (ESI): m/z 461.5 (M+H).

EXAMPLE 27

Preparation of Compound 27: 3-{4-[N'-(3-Methyl-benzylidene)-hydrazino]-6-morpholin-4-yl-pyrimidin-2-yl}-propionic acid ethyl ester Compound 27 was prepared in a similar manner as described in Example 1.

$^1$H NMR (300 MHz, CDCl$_3$), δ (ppm): 8.22 (s, 1H); 7.69(s, 1H); 8.07 (s, 1H); 7.47 (m, 2H); 7.28 (t, J=7.5 Hz, 1H); 7.17 (d, J=7.5 Hz, 1H); 6.23(s, 1H); 4.13 (q, J=7.2 Hz, 2H); 3.78–3.81 (m, 4H); 3.62–3.65 (m, 4H); 2.98 (t, J=7.2 Hz, 2H); 2.77 (t, J=7.2 Hz, 2H); 2.39 (s, 3H); 1.24 (t, J=7.2 Hz, 3H).

MS (ESI): m/z 398.2 (M+H).

EXAMPLE 28

In vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of 5×10$^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test-pyrimidine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with 1×10$^6$ cells/well. The splenocytes were then stimulated with a combination of IFNγ (60 ng/mL) and SAC (0.025%) [or LPS (20 μg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of pyrimidine compounds were tested on human PBMC or THP-1 cells. At least 85 compounds have IC$_{50}$ values of at least 5 μM. Unexpectedly, some of the test compounds have IC$_{50}$ values as low as <1 nM.

EXAMPLE 29

In vivo Assays

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, heat-killed *Myco-* bacterium tuberculosis H37Ra suspended in incomplete Freund's adjuvant. Rats were given a test compound orally once a day for 12 days, starting the day following the induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of pyrimidine compounds of this invention (e.g., Compound 12) reproducibly reduced the arthritic score and delayed the development of polyarthritis in a dose-dependent manner. The arthritis score used in this model was a reflection of the inflammatory state of the structures monitored and the results therefore show the ability of the test compound to provide relief for this aspect of the pathology.

Treatment of Crohn's disease in dinitrobenzene sulfonic acid-induced inflammatory bowel syndrome model rats: Wistar derived male or female rats weighing 200±20 g and fasted for 24 hours were used. Distal colitis was induced by intra-colonic instillation of 2,4-dinitrobenzene sulfonic acid (DNBS, 25 mg in 0.5 mL ethanol 30%) after which air (2 mL) was gently injected through the cannula to ensure that the solution remained in the colon. A test compound and/or vehicle was administered orally 24 and 2 hours before DNBS instillation and then daily for 5 days. One control group was similarly treated with vehicle alone while the other is treated with vehicle plus DNBS. The animals were sacrificed 24 hours after the final dose of test compound administration and each colon was removed and weighed. Colon-to-body weight ratio was then calculated for each animal according to the formula: Colon (g)/BW×100. The "Net" increase in ratio of Vehicle-control+DNBS group relative to Vehicle-control group was used as a base for comparison with test substance treated groups and expressed as "% Deduction." Pyrimidine compounds of this invention (e.g., Compound 12) reproducibly had about 30% deduction. A 30% or more reduction in colon-to-body weight ratio, relative to the vehicle treated control group, was considered significant.

Rats treated with test substance orally showed a marked reduction in the inflammatory response. These experiments were repeated three times and the effects were reproducible.

Treatment of Crohn's disease in CD4$^+$ CD45Rb$^{high}$ T cell-reconstituted SCID colitis model mice: Spleen cells were prepared from normal female BALB/c mice. For cell purification, the following anti-mouse antibodies were used to label non-CD4$^+$ T cells: B220 (RA3-6B2), CD11b (M1/70), and CD8α (53-6.72). All antibodies were obtained from BioSource (Camarillo, Calif.). M450 anti-rat IgG-coated magnetic beads (Dynal, Oslo, Norway) were used to bind the antibodies and negative selection was accomplished using an MPC-1 magnetic concentrator. The enriched CD4$^+$ cells were then labeled for cell sorting with FITC-conjugated CD45RB (16A, Pharmingen, San Diego, Calif.) and PE-conjugated CD4 (CT-CD4, Caltag, Burlingame, Calif.). CD4$^+$ CD$_{45}$RB$_{high}$ cells were operationally defined as the upper 40% of CD45Rb-staining CD4$^+$ cells and sorted under sterile conditions by flow cytometry. Harvested cells were resuspended at 4×10$^6$/mL in PBS and injected 100 μL intraperitoneally into female C.B-17 SCID mice. Pyrimidine compounds of this invention (e.g., Compound 12) and/or vehicle was orally administered once a day, 5 days per week, starting the day following the transfer. The transplanted SCID mice were weighed weekly and their clinical condition was monitored.

Colon tissue samples were fixed in 10% buffered formalin and embedded in paraffin. Sections (4 μm) collected from ascending, transverse, and descending colon were cut and stained with hematoxylin and eosin. The severity of colitis was determined based on histological examination of the distal colon sections, whereby the extent of colonic inflammation was graded on a scale of 0–3 in each of four criteria: crypt elongation, cell infiltration, depletion of goblet cells, and the number of crypt abscesses.

LP lymphocytes were isolated from freshly obtained colonic specimens. After removal of payer's patches, the colon was washed in Ca/Mg-free HBSS, cut into 0.5 cm pieces and incubated twice in HBSS containing EDTA (0.75 mM), DTT (1 mM), and antibiotics (amphotericin 2.5 μg/mL, gentamicin 50 μg/mL from Sigma) at 37° C. for 15 min. Next, the tissue was-digested further in RPMI containing 0.5 mg/mL collagenase D, 0.01 mg/mL DNase I (Boehringer Manheim), and antibiotics at 37° C. LP cells were then layered on a 40–100% Percoll gradient (Pharmacia, Uppsala, Sweden), and lymphocyte-enriched populations were isolated from the cells at the 40–100% interface.

To measure cytokine production, 48-well plates were coated with 10 μg/mL murine anti-CD3ε antibody (145-2C11) in carbonate buffer (PH 9.6) overnight at 4° C. 5×10$^5$ LP cells were then cultured in 0.5 ml of complete medium in precoated wells in the presence of 1 μg/mL soluble anti-CD28 antibody (37.51). Purified antibodies were obtained from Pharmingen. Culture supernatants were removed after 48 h and assayed for cytokine production. Murine IFNγ was measured using an ELISA kit from Endogen (Cambridge, Mass.), according to the manufacturer's instructions.

Histological analysis showed that oral administration of pyrimidine compounds of this invention (e.g., Compound 12) reduced colonic inflammation as compared to vehicle control. The suppressive effect was dose-dependent with a substantial reduction at a dose of 10 mg/kg. The calculated colon-to-body weight ratio was consistent with the histological score, showing attenuation by treatment with the test compound. Furthermore, analysis of cytokines from LP cells in response to anti-CD3 antibody and anti-CD28 antibody demonstrated that LP cells from vehicle control produced an augmented level of IFNγ and treatment with test substance greatly diminished the production. These results clearly demonstrated the potential of the test substance in treatment of inflammatory bowel disease represented by Crohn's disease.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions For example, compounds structurally analogous a pyrimidine compound described in the specification also can be made, screened for their inhibiting IL-12 activities, and used to practice this invention. Thus, other embodiments are also within the claims.

What is claimed is:

1. A method for treating an interleukin-12 overproduction-related disorder, wherein the disorder is rheumatoid arthritis, sepsis, Crohn's disease, multiple sclerosis, psoriasis, or insulin-dependent diabetes mellitus, comprising administering to a subject in need thereof the compound of formula (I):

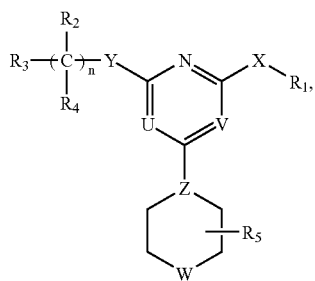

wherein $R_1$ is

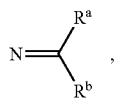

aryl, or heteroaryl;

each of $R_2$ and $R_4$, independently, is $R^c$, halogen, nitro, cyano, isothionitro, $SR^c$, or $OR^c$; or $R_2$ and $R_4$, taken together, is carbonyl;

$R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; $R_5$ is H or alkyl;

n is 0, 1, 2, 3, 4, 5, or 6;

X is O, S, S(O), S(O$_2$), or $NR^c$;

Y is a covalent bond, $CH_2$, C(O), C=N—$R^c$, C=N—$OR^c$, C=N—$SR^c$, O, S, S(O), S(O$_2$), or $NR^c$;

Z is N or CH;

one of U and V is N, and the other is $CR^c$; and

W is O, S, S(O), S(O$_2$), $NR^c$, or $NC(O)R^c$;

in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl; or pharmaceutically acceptable salt thereof.

2. A pharmaceutical composition comprising the compound of formula (I):

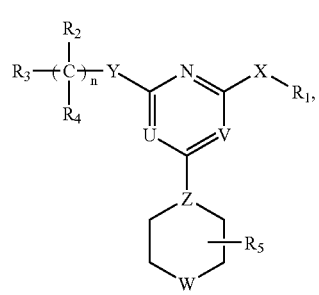

wherein $R_1$ is

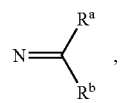

aryl, or heteroaryl;

each of $R_2$ and $R_4$, independently, is $R^c$, halogen, nitro, cyano, isothionitro, $SR^c$, or $OR^c$; or $R_2$ and $R_4$, taken together, is carbonyl;

$R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$;

$R_5$ is H or alkyl;

n is 0, 1, 2, 3, 4, 5, or 6;

X is O, S, S(O), S(O$_2$), or $NR^c$;

Y is a covalent bond, $CH_2$, C(O), C=N—$R^c$, C=N—$OR^c$, C=N—$SR^c$, O, S, S(O), S(O$_2$), or $NR^c$;

Z is N or CH;

one of U and V is N, and the other is $CR^c$; and

W is O, S, S(O), S(O$_2$), $NR^c$, or $NC(O)R^c$;

in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl; or pharmaceutically acceptable salt thereof; and a pharmaceutically acceptable carrier.

3. The pharmaceutical composition of claim 2, wherein $R_1$ is

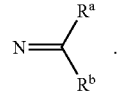

4. The pharmaceutical composition of claim 3, wherein U is N and V is CH.

5. The pharmaceutical composition of claim 3, wherein Z is N and W is O.

6. The pharmaceutical composition of claim 3, wherein X is $NR^c$.

7. The pharmaceutical composition of claim 6, wherein $R^c$ is H, methyl, ethyl, or acetyl.

8. The pharmaceutical composition of claim 3, wherein Y is O or $CH_2$, and n is 0, 1, 2, 3, or 4.

9. The pharmaceutical composition of claim 8, wherein $R_3$ is aryl or heteroaryl.

10. The pharmaceutical composition of claim 9, wherein $R_3$ is pyridinyl.

11. The pharmaceutical composition of claim 8, wherein $R_3$ is $OR^c$, $SR^c$, $C(O)OR^c$, or $C(O)NR^cR^d$.

12. The pharmaceutical composition of claim 8, wherein $R_3$ is

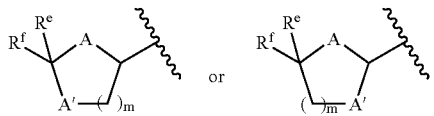

in which
each of A and A', independently, is O, S, or NH;
each of $R^e$ and $R^f$, independently is H, alkyl, aryl, or heteroaryl; and
m is 1 or 2.

13. The pharmaceutical composition of claim 3, wherein one of $R^a$ and $R^b$ is

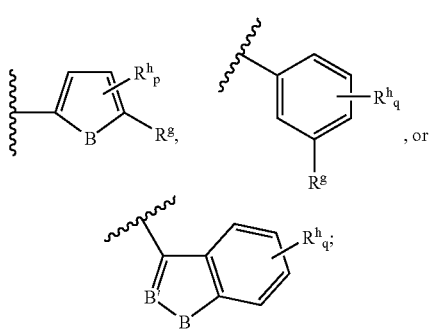

in which
B is $NR^i$, O, or S;
B' is N or $CR^i$;
$R^g$ is H, alkyl, or alkoxyl;
$R^h$ is halogen, $NO_2$, CN, alkyl, aryl, heteroaryl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$;
$R^i$ is H, alkyl, or alkylcarbonyl;
p is 0, 1, or 2; and
q is 0, 1, 2, 3, or 4.

14. The pharmaceutical composition of claim 13, wherein one of $R^a$ and $R^b$ is

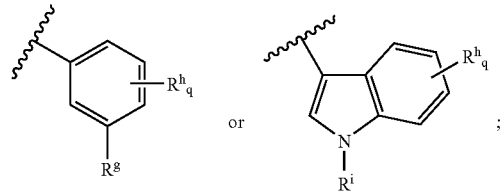

and the other of $R^a$ and $R^b$ is H or alkyl.

15. The pharmaceutical composition of claim 14, wherein $R^g$ is H, methyl, ethyl, propyl, cyclopropyl, methoxy, or ethoxy; $R^h$ is F, Cl, CN, methyl, methoxy, ethoxy, $OC(O)CH_3$, $OC(O)C_2H_5$, $C(O)OH$, $C(O)OC_2H_5$, $C(O)NH_2$, $NHC(O)CH_3$, or $S(O_2)NH_2$; $R^i$ is H, methyl, ethyl, or acetyl, and q is 0, 1, or 2.

16. The pharmaceutical composition of claim 15, wherein $R^g$ is methyl or methoxy; $R^i$ is H; and q is 0.

17. The pharmaceutical composition of claim 15, wherein U is N and V is CH.

18. The pharmaceutical composition of claim 17, wherein Z is N and W is O.

19. The pharmaceutical composition of claim 18, wherein X is $NR^c$; and $R^c$ is H, methyl, ethyl, or acetyl.

20. The pharmaceutical composition of claim 19, wherein Y is O or $CH_2$; and n is 0, 1, 2, 3, or 4.

21. The pharmaceutical composition of claim 20, wherein $R_3$ is aryl or heteroaryl.

22. The pharmaceutical composition of claim 21, wherein $R_3$ is pyridinyl.

23. The pharmaceutical composition of claim 15, wherein Y is O or $CH_2$, and n is 0, 1, 2, 3, or 4.

24. The pharmaceutical composition of claim 23, wherein $R_3$ is aryl or heteroaryl.

25. The pharmaceutical composition of claim 23, wherein $R_3$ is pyridinyl.

26. The pharmaceutical composition of claim 2, wherein $R_1$ is aryl or heteroaryl.

27. The pharmaceutical composition of claim 26, wherein $R_1$ is

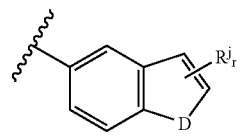

in which
D is O, S, or $NR^m$;
$R^j$ is benzo, halogen, CN, hydroxyl, alkyl, aryl, heteroaryl, alkoxyl, aryloxyl, or heteroaryloxyl;
$R^m$ is H, alkyl, or alkylcarbonyl; and
r is 0, 1, or 2.

28. The pharmaceutical composition of claim 27, wherein X is $NR^c$; and $R^c$ is H, methyl, ethyl, or acetyl.

29. The pharmaceutical composition of claim 28, wherein U is N and V is CH.

30. The pharmaceutical composition of claim 29, wherein Z is N and W is O.

31. The pharmaceutical composition of claim 30, wherein Y is O or $CH_2$; and n is 0, 1, 2, 3, or 4.

32. The pharmaceutical composition of claim 27, wherein Y is O or $CH_2$; and n is 0, 1, 2, 3, or 4.

33. The pharmaceutical composition of claim 32, wherein $R_3$ is aryl or heteroaryl.

34. The pharmaceutical composition of claim 33, wherein $R_3$ is pyridinyl.

35. The pharmaceutical composition of claim 32, wherein $R_3$ is $OR^c$, $SR^c$, $C(O)OR^c$ or $C(O)NR^cR^d$.

36. The pharmaceutical composition of claim 32, wherein $R_3$ is

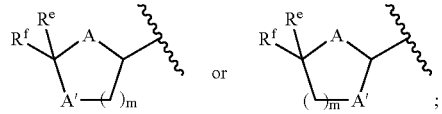

in which
each of A and A', independently, is O, S, or NH;
each of $R^e$ and $R^f$, independently, is H, alkyl, aryl, or heteroaryl; and
m is 1 or 2.

37. The pharmaceutical composition of claim 32, wherein R₁ is

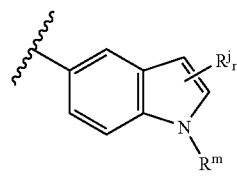

38. The pharmaceutical composition of claim 37, wherein R$^j$ is methyl, ethyl, propyl, or benzo; and r is 1 or 2.

39. The method of claim 1, wherein the disorder is rheumatoid arthritis.

40. The method of claim 1, wherein the disorder is Crohn's disease.

41. The method of claim 1, wherein the disorder is multiple sclerosis.

42. The method of claim 1, wherein the disorder is psoriasis.

43. The method of claim 1, wherein the disorder is diabetes mellitus.

44. The method of claim 1, wherein the disorder is sepsis.

45. The method of claim 1, wherein the compound of formula (I) is:

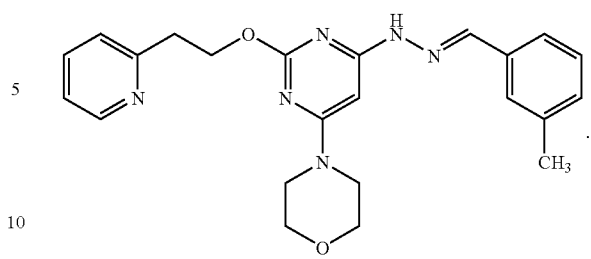

46. The pharmaceutical composition of claim 2, wherein the compound of formula (I) is:

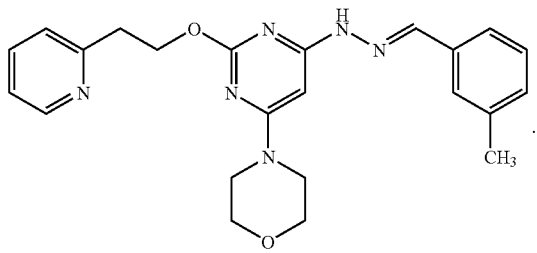

* * * * *